United States Patent [19]
Strickland

[11] Patent Number: 5,387,222
[45] Date of Patent: Feb. 7, 1995

[54] CARPAL TUNNEL TOME AND CARPAL TUNNEL RELEASE SURGERY

[76] Inventor: James W. Strickland, 7979 S. 1000 East, Zionsville, Ind. 46077

[21] Appl. No.: 61,855

[22] Filed: May 14, 1993

[51] Int. Cl.$^6$ .............................................. A61B 17/32
[52] U.S. Cl. ....................................... 606/167; 30/294
[58] Field of Search ................. 606/167, 170; 128/858; 30/289, 294

[56] References Cited

U.S. PATENT DOCUMENTS

| | | | |
|---|---|---|---|
| 3,365,798 | 1/1968 | Cunningham | 606/167 |
| 3,831,274 | 8/1974 | Horrocks | 30/294 |
| 3,975,822 | 8/1976 | Mabus | 30/294 |
| 4,026,295 | 5/1977 | Lieberman | 606/167 |
| 4,962,770 | 10/1990 | Agee et al. | |
| 5,029,573 | 7/1991 | Chow | |
| 5,273,024 | 12/1993 | Menon et al. | 128/898 |

FOREIGN PATENT DOCUMENTS 2203341 10/1988 United Kingdom ................ 606/167

OTHER PUBLICATIONS

David M. Pagnanelli, M.D. et al., "Bilateral Carpal Tunnel Release at One Operation: Report of 228 Patients", *Neurosurgery,* vol. 31, No. 6, Dec. 1992.
David M. Pagnanelli, M.D. et al., "Carpal tunnel syndrome: surgical treatment using the Paine retinaculatome", *J. Neurosurg.,* vol. 75, Jul. 1991.
Kenneth W. E. Paine, M.D. et al., "Decompression using the Paine retinaculotome", *J. Neurosurg.,* vol. 59, Dec. 1983.
Ruggles Corporation Catalog, R-520 PAINE's Carpal Tunnel Retinaculotome, p. 59.

*Primary Examiner*—Stephen C. Pellegrino
*Assistant Examiner*—William Lewis
*Attorney, Agent, or Firm*—Woodard, Emhardt, Naughton Moriarty & McNett

[57] ABSTRACT

A carpal tunnel tome for performing carpal tunnel release surgery includes a slender handle with a blade at one end. The blade is bounded on both sides by a pair of relatively blunt protuberances that extend distally beyond the cutting edge of the blade. The protuberances allow the instrument to straddle the ligament and serve to protect surrounding tissue during the cutting procedure of the ligament. The surgical procedure utilizing the tome requires only a single small incision in the palm of the patient's hand adjacent the distal end of the transverse carpal ligament. The instrument is then placed in the incision straddling the ligament and is then advanced proximately toward the patient's wrist until the transverse carpal ligament is completely divided. The instrument is then withdrawn and the incision is closed with one or two sutures and an appropriate dressing is applied.

9 Claims, 6 Drawing Sheets

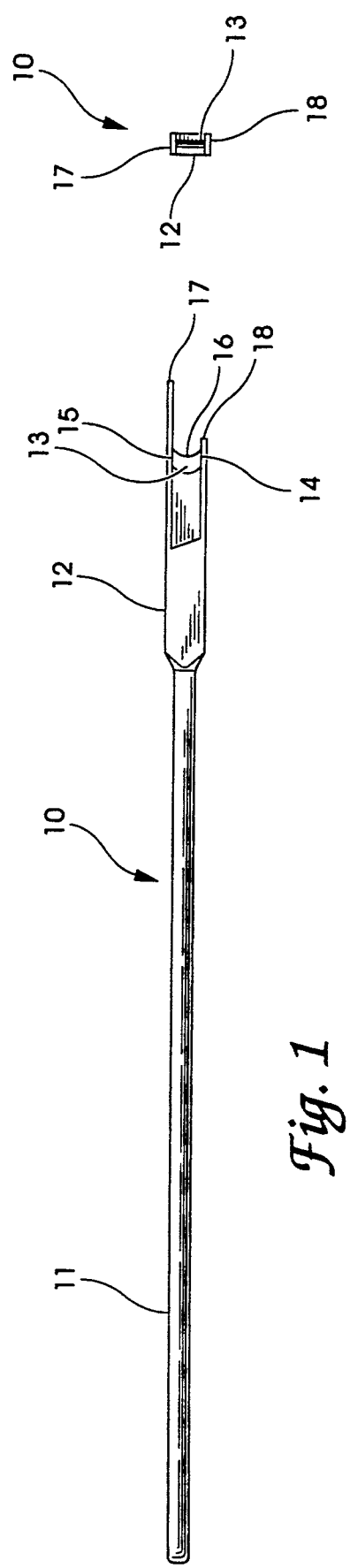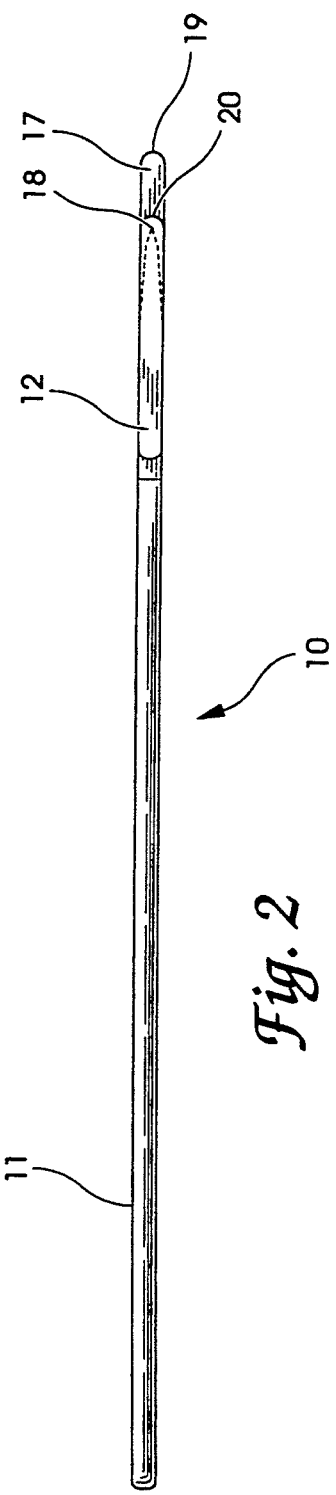

CARPAL TUNNEL TOME AND CARPAL TUNNEL RELEASE SURGERY

BACKGROUND OF THE INVENTION

The present invention relates generally to surgery, and in particular to the use of a carpal tunnel tome to perform carpal tunnel release surgery.

Surgical decompression of the carpal tunnel, which is often referred to as carpal tunnel release surgery, is the most commonly performed surgical procedure in the United States. The condition is frequent in middle-aged persons whose job requires exposure to vibrating tools or chronic, repetitious use of the hands, such as on keyboards or on assembly lines. Carpel tunnel syndrome is normally characterized by some combination of wrist pain, forearm aching, and/or pain, tingling and numbness in the thumb, index and middle fingers. The pain results from compression of the median nerve in an anatomic passageway in the wrist and palm that is frequently referred to as the carpal tunnel.

Historically, the operative procedure designed to eliminate the symptons of carpal tunnel syndrome includes making an incision in the palm—sometimes extending across the wrist—to divide the deep transverse carpel ligament and its proximal fascial extension, and release the pressure on the median nerve. Although the procedure has been highly successful in relieving most patients' symptons, it is often complicated by tenderness around the incision site in the proximal palm and across the wrist. In addition, patients frequently experience "pillar pain" at the base of the thenar and hypothenar eminences, just distal to the wrist crease and on each side of the surgical scar. This post-surgical discomfort has been implicated as the cause for the slow return of patients to occupational activities following conventional carpal tunnel release surgery.

In recent years, there have been efforts made to alter the technique of carpal tunnel release surgery in an effort to minimize the amount of proximal palm and pillar pain, and allow patients to resume normal occupational and domestic activities more quickly. One such method involves making a relatively shorter incision located entirely in the palm and then dividing the deep transverse carpal ligament by straddling the ligament with small blunt scissors which are passed proximately toward the patient's wrist. Although this technique is effective, there is some danger of inadvertent injury to the median nerve or other structures from the tip of the scissors as they are blindly passed in a proximal direction. Further, the length of incision required in order to divide the majority of the ligament prior to scissor passage, may still be large enough to lead to some palmar pain.

The use of one of several endoscopic methods for division of the deep transverse carpal ligament has also received considerable popularity during the past several years. These techniques employ the passage of a special instrument beneath the carpal ligament, such as for example, the method shown in U.S. Pat. No. 5,029,573 to Chow, and then utilize fiberoptics and special cutting instruments to observe and divide the ligament. Although efforts have been made to make these techniques as simple and safe as possible, they still require specialized training and a reasonably long learning curve before the surgeon becomes adept at their use. Complications such as injury to or division of, the median nerve, one of its branches, the tendons within the carpal vault or the superficial arterial arch of the palm have been described with disconcerting frequency. In some reported cases, the instrument has actually been passed into the wrong passageway where injury may occur to the ulnar nerve or artery. Endoscopic carpal tunnel release surgery averages from 30 to 60 minutes for completion and can be done under either a general or local anesthesia. Apart from being a rather lengthy procedure, endoscopic techniques have been challenged as not always being consistent in their ability to completely divide the transverse carpal ligament.

What is needed is a simple, safe and effective technique for division of the deep transverse carpal ligament that requires only a small mid-palmar incision and utilizes a small cutting instrument designed to protect adjacent tissues when cutting the ligament.

SUMMARY OF THE INVENTION

In an effort to respond to this need, the present invention comprises a method of performing carpal tunnel release surgery that is designed to be carried out under local anesthesia and should require less than 10 minutes to complete. The first step in the surgery involves making a relatively short incision in the patient's palm adjacent the distal edge of the transverse carpal ligament. The incision and underlying adipose tissue are then retracted until the distal portion of the transverse carpal ligament is visible. Next, a carpal tunnel tome having a blade shielded on its ends by a pair of blunt protuberances projecting away from the blade is provided. The carpal tunnel tome is then positioned in the incision so that the protuberances straddle the transverse carpal ligament and the blade is positioned against the ligament. The carpal tunnel tome is then advanced toward the patient's wrist until the transverse carpal ligament is completely divided. Finally, the carpal tunnel tome is withdrawn from the patient and the incision is typically closed with one to two sutures.

Apart from the surgical method, the present invention is also directed to the carpal tunnel tome itself. The tome comprises an elongated slender handle having a blade attached to its distal end. The blade has a cutting edge pointing distally away from the distal end of the handle and is concealed between a pair of relatively blunt protuberances that are attached on either side of the blade and extend distally beyond the cutting edge.

One object of the present invention is to provide an improved instrument and method for performing carpal tunnel release surgery.

Another object of the present invention is to provide a surgical method that results in less trauma to the patient and quicker post-operative recovery.

Related objects and advantages of the present invention will be apparent from the following description.

BRIEF DESCRIPTION OF THE DRAWINGS

FIGS. 1-3 are side, bottom and end views, respectively of an orthographic projection of a carpal tunnel tome according to the preferred embodiment of the present invention.

DESCRIPTION OF THE PREFERRED EMBODIMENT

Figure 4:
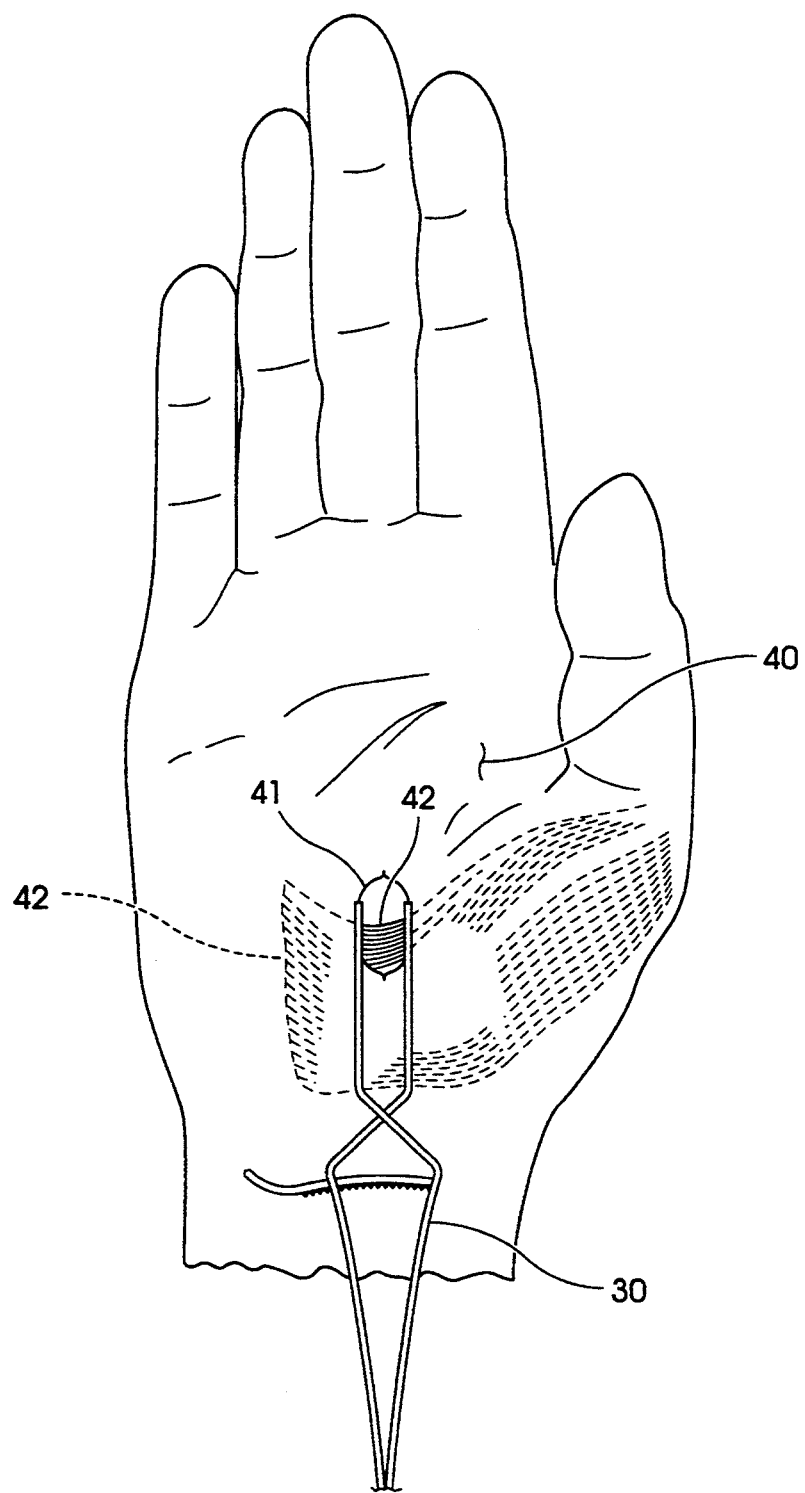
FIGS. 4-6 and 8-9 are views of the palmar side of a patient's hand and wrist showing serially the carpal tunnel release surgery according to the technique of the present invention.

For the purposes of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

Referring now to FIGS. 1–3, a carpal tunnel tome 10 according to the present invention includes a slender cylindrical handle 11 having a head portion 12 integrally formed thereon. If desired or deemed necessary, handle 11 and head portion 12 could be formed separately and attached to one another by one of several means known in the art. The head portion includes a blade 13 having a cutting edge 16 which is bounded on one side 15 by a relatively blunt protuberance 17 and on its other side 14 by another but shorter blunt protuberance 18. Cutting edge 16 is preferably concave as shown but could also take on other shapes, such as, for example, a slant or V-shape. Both blunt protuberances 17 and 18 project distally beyond cutting edge 16 so that blade 13 is concealed within a channel defined by the blunt protuberances. Head portion 12 is made to have a sufficient width that both blunt protuberances 17 and 18 are provided with rounded distal ends 19 and 20, respectively. In the preferred embodiment, blunt protuberance 17 extends roughly 7 mm distally beyond the other blunt protuberance 18. The reason for this preference will become better understood in reference to the surgical technique utilizing tome 10 described infra.

Another key feature to tome 11 is that blade 13 preferably has a width on the order of about 3 mm, which corresponds roughly to the thickness of the transverse carpal ligament in most adults. Finally, blunt protuberances 17 and 18 are preferably relatively flat surfaces oriented parallel to one another, with each having sufficient thickness to avoid the danger of accidental cutting or damage to tissue contacted by the blunt protuberances. In the preferred embodiment, blunt protuberances 17 and 18 have a thickness on the order of about 1 mm.

As can be seen from FIGS. 1–3, the head 12 and the portion of the handle 11 contiguous to the head 12 have dimensions in height and width which are no greater than the dimensions in cross section of the blade 16 protuberances 17 and 18.

Operative Procedure

The patient is brought to an outpatient operating room where approximately 10 cc of local anesthetic agent are infiltrated under the proximal palmar skin, across the wrist crease and into the sub fascial wrist compartment. Additional anesthetic material is also infiltrated directly into the carpal tunnel. Under tourniquet control, a 1–2 cm incision 41 is made between the thenar and hypothenar creases at the base of the distal edge of the thenar musculature on the palmar side 40 of the patient's hand as shown in FIG. 4. Sharp dissection is carried down to provide exposure, and a small Holzheimer self-retracting instrument 30 is usually repositioned several times as increasing depth of the incision is created by sharp and blunt dissection. A surgical sponge (not shown) may also be used to further clarify the level of dissection until the distal portion of the deep transverse carpal ligament 42 is clearly visualized through the incision, and all overhanging adipose tissue retracted.

Figure 5:
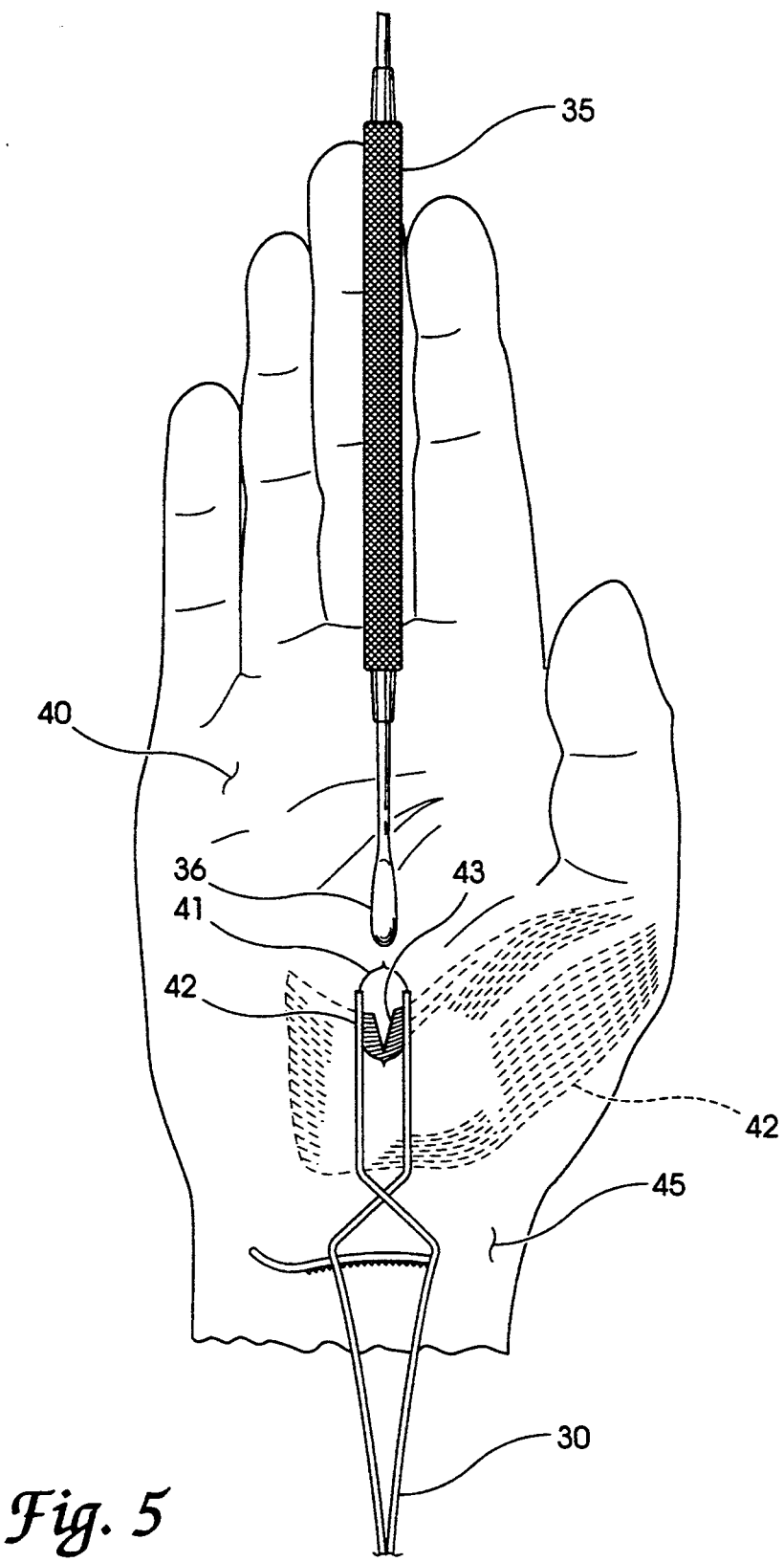

Referring now to FIG. 5, in the preferred method, the distal 1½ cm portion 43 of the ligament is then sharply divided, exposing the contents of the carpal vault. The curved end 36 of a Freer elevator 35 is then placed beneath the partially divided ligament and gently passed proximally toward the patient's wrist 45 for 3–4 cm to separate the contents of the carpal tunnel from the ligament 42. Similarly, the Freer elevator may be passed on the palmar surface of ligament 42 to separate any fascial connections.

Figure 6:
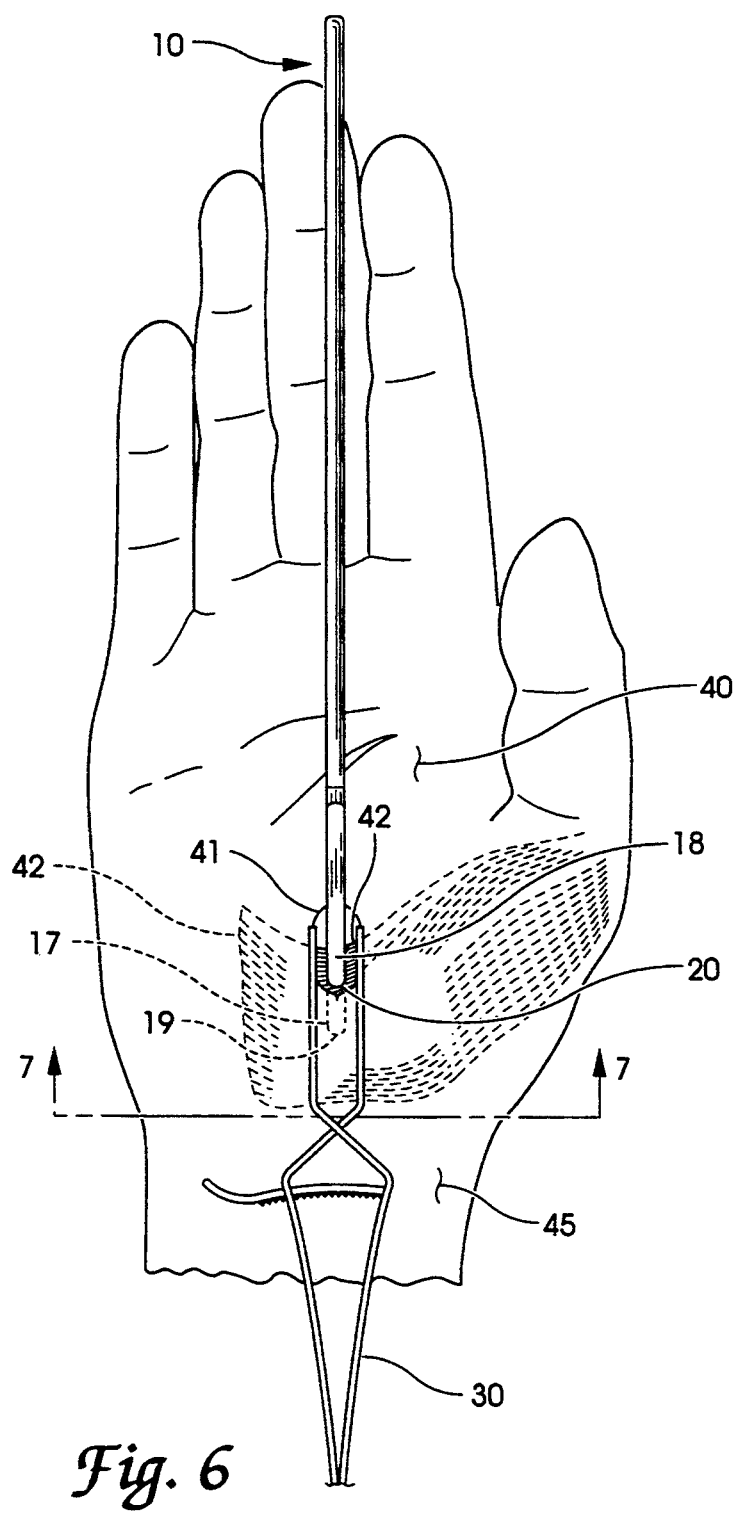
Figure 7:
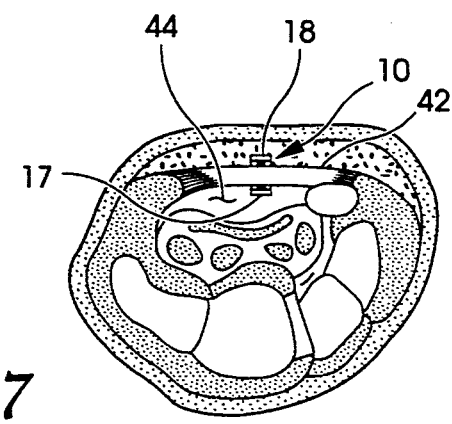
FIG. 7 is a cross-section through the patient's wrist at a midpoint in the surgery looking in the direction of arrows 7—7 of FIG. 6.
Figure 8:
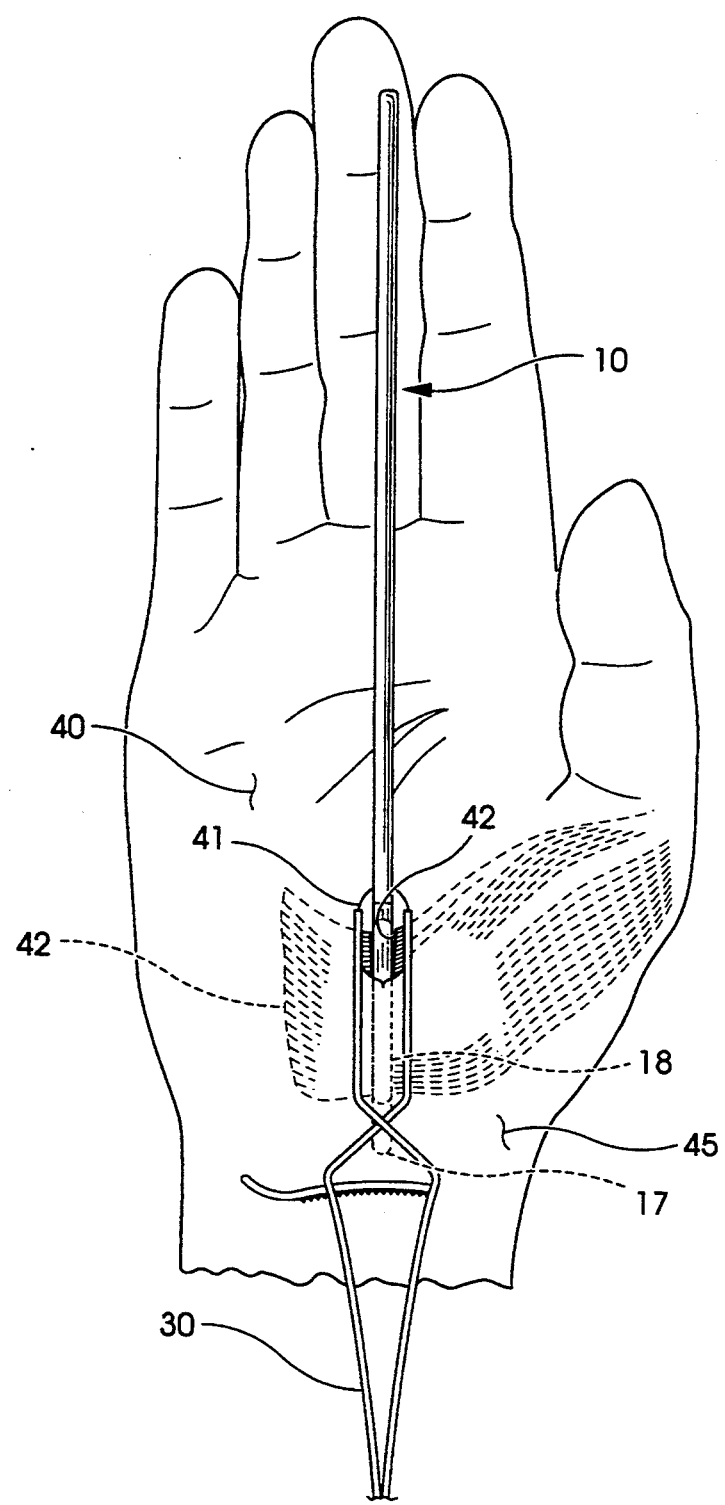
Figure 9:
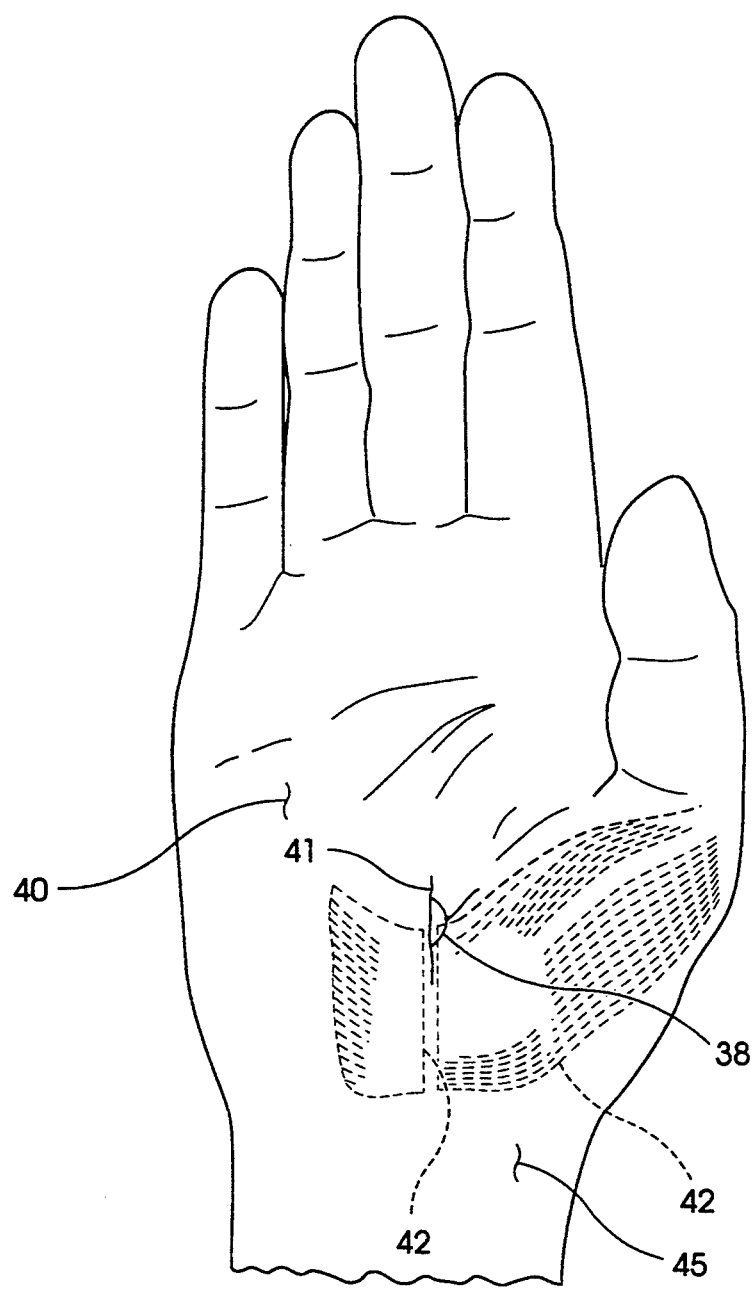

Next, as shown in FIGS. 6–8, the carpal tunnel tome 10 is inserted into the wound with exposure being maintained by the Holzheimer self-restraining retractor 30. A small right-angle retractor (not shown) is preferably placed in the proximal aspect of the wound so that the leading protuberance 17 of tome 10 can be accurately placed beneath ligament 42 under direct vision. Once the surgeon is certain that blunt protuberances 17 and 18 are straddling ligament 42, the carpal tunnel tome is passed proximally for 3–4 cm or until a definite lessening of resistance is felt. At this point, the tome 10 is withdrawn from the small wound allowing the surgeon to directly view the carpal tunnel 44 (FIG. 7) and confirm the gapping between the radial and ulnar edges of the divided ligament; this allows the surgeon to confirm that the ligament 42 has been completely divided and the median nerve decompressed. Gently teasing the nerve to be sure that it is soft and nonadherent may then be carried out and a limited inspection of the carpal vault for any underlying lesions may also be done. After the wound has been irrigated, one or two sutures 38 are then used to close incision 41 as shown in FIG. 9. A small compressive dressing (not shown) is then applied from the distal forearm to the mid-palm, and the patient is encouraged to vigorously move his or her fingers.

By maintaining the position of the longer blunt protuberance 17 of instrument 10 against the under-surface of ligament 42 as the instrument is advanced proximally, safety for the median nerve and palmar tendons is assured and the complete division of the ligament and its proximal fascial continuations is reliably achieved. Unlike the "blind" release afforded by endoscopic instruments, the relatively short mid-palmar incision of the present technique allows exposure and observation of the median nerve and the contents of the carpal vault, and allows for direct visual confirmation of the complete release of the ligament and expansion of the carpal tunnel.

After the surgery, the patient generally returns to the office in 10–14 days for suture removal. Early clinical results have indicated that the present technique results in markedly diminished palmar pain, with palmar pain discomfort and pillar pain being similar to that seen following endoscopic carpal tunnel release surgery. It is believed that the present technique results in less trauma to the patient and results in quicker post-operative recovery so that the patient is actually able to return to work at an earlier time than that possible with the techniques of the prior art. There is every reason to believe that the method of the present invention provides results which are entirely comparable with endoscopic carpal tunnel release surgery, except with less palmar discomfort and earlier return to occupational and domestic activities.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

I claim:

1. A method of performing carpal tunnel release surgery comprising the steps of:
   making an incision in the patient's palm adjacent the distal edge of the transverse carpal ligament;
   retracting the incision until the distal portion of the transverse carpal ligament is visable;
   providing a carpal tunnel tome having a blade shielded on its ends by a pair of blunt protuberances projecting away from the blade;
   positioning a portion of the carpal tunnel tome in the incision so that protuberances straddle the transverse carpal ligament and the blade is positioned against the ligament;
   advancing the carpal tunnel tome toward the patient's wrist until the transverse carpal ligament is completely divided; and
   withdrawing the carpal tunnel tome from the patient.

2. The method of claim 1 further comprising the step of inserting an instrument through the incision and into the carpal tunnel to separate adjacent tissue from the under-surface of the transverse carpal ligament before said positioning step.

3. The method of claim 2 further comprising the step of dividing the distal portion of the transverse carpal ligament before said step of inserting an instrument.

4. The method of claim 3 wherein the distal portion is about 1 to 1½ centimeters wide.

5. The method of claim 1 further comprising the step of inserting an instrument through the incision along the upper surface of the transverse carpal ligament to separate any fascial connections.

6. The method of claim 1 further comprising the step of applying a local anesthetic to the patient's palm and wrist before said step of making an incision.

7. The method of claim 1 wherein said incision is made substantially perpendicular to the distal edge of the transverse carpal ligament between the thenar and hypothenar creases of the patient's palm.

8. The method of claim 7 wherein the incision is made about 1 to 2 centimeters long.

9. The method of claim 1 wherein said advancing step includes maintaining one of the protuberances of the carpal tunnel tome in contact with the under-surface of the transverse carpal ligament to prevent accidental cutting of the median nerve and other sensitive tissue within the carpal tunnel.

* * * * *